United States Patent [19]
Aga et al.

[11] Patent Number: 5,338,420
[45] Date of Patent: Aug. 16, 1994

[54] PROCESS FOR PREPARING HIGH α-GLYCOSYL-L-ASCORBIC ACID, AND SEPARATION SYSTEM FOR THE PROCESS

[75] Inventors: Hajime Aga; Masaru Yoneyama; Shuzo Sakai, all of Okayama, Japan

[73] Assignee: Kabushiki Kaisha Hayashibara Seibutsu Kagaku Kenkyujo, Okayama, Japan

[21] Appl. No.: 990,081

[22] Filed: Dec. 14, 1992

[30] Foreign Application Priority Data

Jan. 30, 1992 [JP] Japan .................. 4-057617

[51] Int. Cl.⁵ .............................. C25B 3/00
[52] U.S. Cl. .................. 204/182.6; 204/182.4
[58] Field of Search .......... 204/182.4, 182.6

[56] References Cited

U.S. PATENT DOCUMENTS

4,767,870  8/1988  Fujiwara et al. .................. 549/315

FOREIGN PATENT DOCUMENTS

0398484  11/1990  European Pat. Off. ...... C12P 19/58
0425066   5/1991  European Pat. Off. ...... C12P 19/60
0018858   9/1972  Japan .................. 204/182.4
3183492   8/1991  Japan .................. C12P 19/58

OTHER PUBLICATIONS

K. Ideue, "Desalt Used Ion-Exchange Membranes," *Up-to-date Food processing*, vol. 21, No. 7, Jul. 1986 pp. 54–57.

*Primary Examiner*—Kathryn Gorgos
*Attorney, Agent, or Firm*—Browdy and Neimark

[57] ABSTRACT

A high α-glycosyl-L-ascorbic acid content product is prepared by subjecting an aqueous solution containing α-glycosylL-ascorbic acid together with L-ascorbic acid and/or a saccharide to electrodialysis wherein an anion-exchange membrane is used in order to allow the L-ascorbic acid to predominantly permeate the membrane and to separate the L-ascorbic acid from α-glycosyl-L-ascorbic acid, or in order to allow the α-glycosyl-L-ascorbic acid to predominantly permeate the membrane and to separate the α-glycosyl-L-ascorbic acid from the saccharide. Thus, a high α-glycosyl-L-ascorbic acid content product having a desirable stability and physiological activity is readily prepared.

10 Claims, 1 Drawing Sheet

PROCESS FOR PREPARING HIGH α-GLYCOSYL-L-ASCORBIC ACID, AND SEPARATION SYSTEM FOR THE PROCESS

BACKGROUND OF THE INVENTION

1. Field of the invention

The present invention relates to a process for preparing a high α-glycosyl-L-ascorbic acid content product and separation system for said process, more particularly, to a process for preparing a high α-glycosyl-L-ascorbic acid content product from an aqueous solution containing α-glycosyl-L-ascorbic acid together with other concomitants such as L-ascorbic acid and a saccharide, and to a separation system for said process.

2. Description of the prior art

As disclosed in Japanese Patent Laid-Open Nos. 135,992/91 and 139,288/91, α-glycosyl-L-ascorbic acid is a saccharide derivative of L-ascorbic acid which has the chemical structure as shown in Formula 1, and, unlike L-ascorbic acid, exhibits no direct reducing activity and has a satisfiable stability, as well as being readily hydrolyzed in vivo to exert the inherent activity of L-ascorbic acid.

Formula 1:

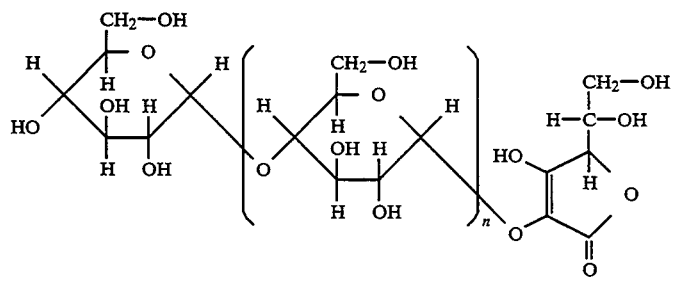

wherein the symbol "n" means "0" or "an integer" selected from 1 to 6.

As disclosed in Japanese Patent Laid-Open Nos.135,992/91 and 183 492/91 the preparation of α-glycosyl-L-ascorbic acid is effected by subjecting an aqueous solution containing L-ascorbic acid and an α-glucosyl saccharide to the action of a saccharide-transferring enzyme with or without glucoamylase.

The reaction mixture thus obtained contains a relatively-low amount of the α-glycosyl-L-ascorbic acid and relatively-large amounts of other concomitants such as L-ascorbic acid and saccharides.

In order to prepare a high α-glycosyl-L-ascorbic acid content product from the reaction mixture, adsorption and desorption using an anjou-exchange resin, and column chromatography using a cation-exchange resin is used have been known.

The adsorption and desorption is a purification method which comprises demineralizing a reaction mixture with a cation-exchange resin (H+-form) allowing the resultant demineralized solution to adsorb on an anion-exchange resin (OH⁻-form), washing the anion-exchange resin with water to remove saccharides such as D-glucose and α-glucosyl saccharide, and eluting the substances adsorbed on the anion-exchange resin with an acid- or salt-solution.

The method, however, has drawbacks in that it has a complicated step and requires relatively-large amounts of water, eluate and agent for regeneration; and that the concentration and the yield of the resultant α-glycosyl-L-ascorbic acid are relatively low.

It was found that column chromatography wherein a cation-exchange resin is used has a drawback in that it requires a relatively-large amount of water to effect separation of ingredients, and because of this the objective α-glycosyl-L-ascorbic acid solution is diluted and the production cost increases.

There has been a great demand to establish an industrial-scale preparation process for a high α-glycosyl-L-ascorbic acid content product from an aqueous solution containing α-glycosyl-L-ascorbic acid together with other concomitants such as L-ascorbic acid and saccharides.

SUMMARY OF THE INVENTION

The present inventors have studied membrane separation techniques in order to establish an industrial-scale preparation of a high α-glycosyl-L-ascorbic acid content product from an aqueous solution containing α-glycosyl-L-ascorbic acid together with concomitants such as L-ascorbic acid and saccharides.

As a result, the present inventors found that a high α-glycosyl-L-ascorbic acid content product is readily prepared by subjecting an aqueous solution containing α-glycosyl-L-ascorbic acid together with L-ascorbic acid and/or a saccharide to electrodialysis wherein an anion-exchange resin is used, and that the separation method is industrially advantageous because it provides a high α-glycosyl-L-ascorbic acid content product at a relatively-high concentration and in a relatively-high yield. Furthermore, the present inventors established an industrial-scale separation-system for a preparation of a high α-glycosyl-L-ascorbic acid content product. Thus, we accomplished this invention.

BRIEF EXPLANATION OF THE ACCOMPANYING DRAWING

FIG. 1 shows an example of a separation system according to the present invention.

Throughout the figure, the symbol "1" shows a container capable of holding a solution; the symbol "2", a material feed-cell; the symbol "3" a permeation cell; the symbol "4", an anion-exchange membrane; the symbol "5", a cathode; the symbol "6", an anode; the symbol "7", a power supply connected to a cathode; and the symbol "8", a power supply connected to an anode.

DETAILED DESCRIPTION OF THE INVENTION

Figure 1:
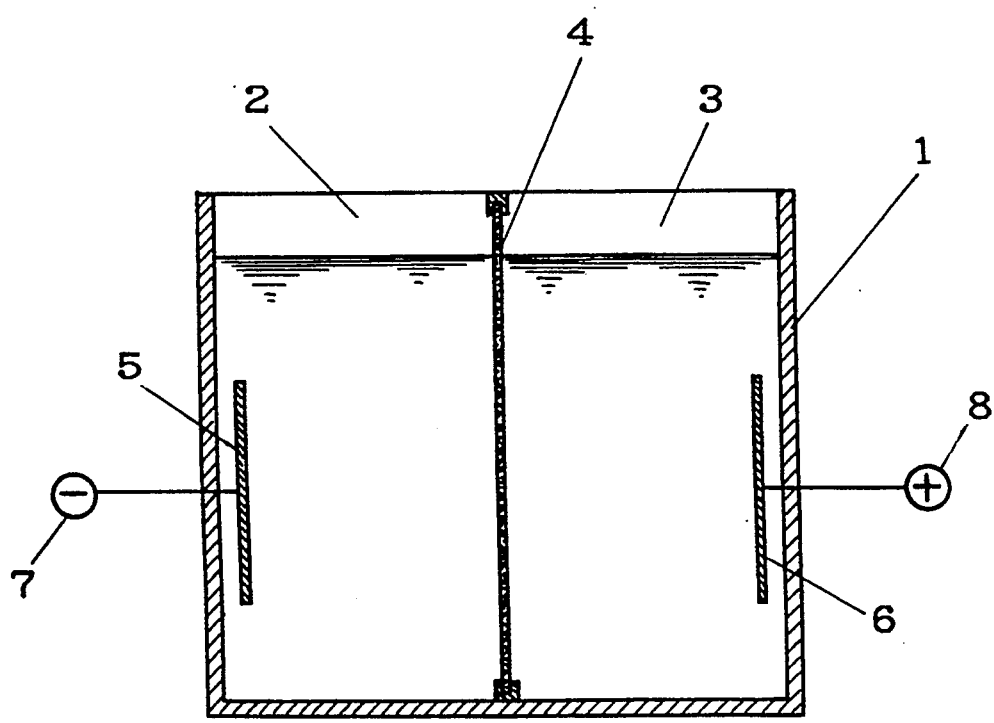

The present invention relates to a process for preparing a high α-glycosyl-L-ascorbic acid content product and separation system for said process, more particularly to a process for preparing a high α-glycosyl-L-ascorbic acid content product from an aqueous solution containing α-glycosyl-L-ascorbic acid together with other concomitants such as L-ascorbic acid and a saccharide, and to a separation system for said process.

The wording "L-ascorbic acid" as referred to in the invention means an L-ascorbic acid in the form of free acid and salts such as alkaline metals and alkaline-earth metals and mixtures thereof, as long as they do not cause any inconvenience.

Similarly as the wording "L-ascorbic acid", the wording "α-glycosyl-L-ascorbic acid" means an α-glycosyl-L-ascorbic acid in the form of free acid and salts as long as they do not cause any inconvenience.

In the electrodialysis employed in the invention, L-ascorbic acid and α-glycosyl-L-ascorbic acid can be recovered in the form of salts or free acid, i.e. demineralized form, to meet to their final use.

The material-feed solutions usable in the invention are aqueous solutions containing α-glycosyl-L-ascorbic acid together with L-ascorbic acid and/or a saccharide. For example, as disclosed in Japanese Patent Laid-Open No.139,288/91, a reaction mixture, which is prepared by subjecting a solution containing an α-glycosyl saccharide and L-ascorbic acid to the action of a saccharide-transferring enzyme with or without glucoamylase, can be advantageously used.

As regards an α-glycosyl-L-ascorbic acid formed via the action of a saccharide-transferring enzyme, it has an α-D-glycopyranosyl group coupled to the alcohol group at the number two carbon atom of L-ascorbic acid moiety, said α-D-glycopyranosyl group consisting of 1 to 7 glucosyl groups linked in α-1,4 fashion. Examples of such an α-glycosyl-L-ascorbic acid are 2-O-α-D-glucopyranosyl-L-ascorbic acid, 2-O-α-D-maltosyl-L-ascorbic acid, 2-O-α-D-maltotriosyl-L-ascorbic acid, 2-O-α-D-maltotetraosyl-L-ascorbic acid, 2-O-α-D-maltopentaosyl-L-ascorbic acid, 2-O-α-D-maltohexaosyl-L-ascorbic acid. acid and 2-O-α-D-maltoheptaosyl-L-ascorbic acid.

The number of the α-D-glucosyl groups is varied varies depending on a saccharide-transferring enzyme used, and, usually cyclomaltodextrin glucanotransferase (EC 2.4.1.19) gives the highest number and a wide distribution of 1 to 7 α-D-glucosyl groups, while α-amylase (EC 3.2.1.1 ) gives a distribution of 1 to 5 α-D-glucosyl groups, and α-glucosidase (EC 3.2.1.20), a distribution of 1 to 4 α-D-glucosyl groups.

As described above, solutions containing α-glycosylL-ascorbic acid, which are formed by a variety of methods, usually contain α-glycosyl-L-ascorbic acid together with relatively-large amounts of concomitants such as intact L-ascorbic acid, D-glucose and α-glucosyl saccharides.

In order to prepare a high α-glycosyl-L-ascorbic acid content product from the solutions, separation methods can be used, wherein the differences of molecular weights and the ionicities of α-glycosyl-L-ascorbic acid and concomitants such as intact L-ascorbic acid and saccharides are utilized. More particularly, it was found that the electrodialysis employed in the invention recovers the objective α-glycosyl-L-ascorbic acid at a relatively-high concentration and in a relatively-high yield, as well as facilitating the realization of an industrial-scale preparation of α-glycosyl-L-ascorbic acid.

In the present invention, L-ascorbic acid and α-glucosyl saccharides which are separated in the electrodialysis can be advantageously used repeatedly as a material for the next saccharide-transfer reaction.

After completion of a saccharide-transfer reaction and before electrodialysis, the resultant reaction mixture can be advantageously subjected to two or more purification methods, for example, a membrane treatment wherein the reaction mixture is subjected to a membrane filter to remove the remaining enzyme, a heat treatment wherein the reaction mixture is heated and the resultant insoluble substances are removed, and a treatment wherein the reaction mixture is subjected to an activated charcoal to remove amylaceous- and colored-substances.

If necessary, other purification methods, for example, adsorption and desorption wherein an anion-exchange resin is used for removing saccharides, and column chromatography wherein a cation-exchange resin is used for removing L-ascorbic acid, can be advantageously used in combination.

In the case of subjecting a material feed-solution to electrodialysis, the solution is usually adjusted to pH 8 or lower, preferably, a pH of about 2–7 in order to prevent undesirable decompositions of α-glycosyl-L-ascorbic acid, L-ascorbic acid and saccharides.

The electrodialysis employed in the present invention will be described hereinafter.

As described in *Up-to-date Foodprocessing*, Vol.21, No.7, pp.54–57 (1986) the electrodialysis using an ion-exchange membrane per se has been known.

In general, an apparatus for electrodialysis is used, which comprises a container capable of holding a solution, cation- and anion-exchange membranes alternately arranged in the container to form cells, a pair of anode and cathode provided in the cells of both ends of the container, as well as being provided apart from the membranes, and a DC power supply connected to the electrodes.

The ion-exchange membranes usable in the invention are, for example, high-molecular organic membranes which are mainly composed of styrene-divinyl copolymers and synthetic fibers as a reinforcing agent. The cation-exchange membranes usable in the invention are usually those which have a sulfonic acid group in order to exhibit a selective cation-permeability.

The anion-exchange membranes usable in the invention are usually those which have a quaternary ammonium salt group in order to exhibit a selective anion-permeability.

The electrodes usable in the invention are placed in electrode cells which are usually filled with an electrolytic solution, e.g. an about 0.1–2N salt solution.

It is, however, difficult to predict whether electrodialysis wherein an ion-exchange membrane is used is actually employable or not as in regards to food materials because the ingredients and properties of a material feed-solution strongly influence the feasibility. In this regard, it is described at page 55, the middle column, lines 6–9 in the above-identified publication that "The ingredients of materials for food industry are complicated, and this requires a confirmation of whether an ion-exchange membrane is fouled or not by a natural organic-compound contained in a material feed-solution."

It was found in the present invention that electrodialysis wherein an ion-exchange membrane is used is employable in a preparation of a high α-glycosyl-L-ascorbic acid content product without causing troubles such as fouling, and that the electrodialysis prepares α-glycosyl-L-ascorbic acid at a relatively-high concentration and in a relatively-high yield.

It was also found that electrodialysis wherein an ion-exchange membrane is used does not necessarily require a cation-exchange membrane, and even in the case of using such a cation-exchange membrane the selection thereof is not necessarily restricted as long as it can inhibit the permeation of coexisting saccharides, while the use of an anion-exchange membrane is inevitable and the selection thereof is important, i.e. those having a molecular weight cut-off in the range of about 100–1 000 are suitably used.

In the case of separating α-glycosyl-L-ascorbic acid from L-ascorbic acid, it was found that an anion-exchange membrane selected from those having a molecular weight cut-off in the range of about 100–200 and being capable of allowing L-ascorbic acid to predominantly permeate is suitably used, and in the case of separating α-glycosyl-L-ascorbic acid from saccharides an anion-exchange membrane selected from those having a molecular weight cut-off in the range of about 200–1,000 and being capable of allowing α-glycosyl-L-ascorbic acid to predominantly permeate is suitably used.

The present separation system for preparing a high α-glycosyl-L-ascorbic acid content product and its use will be explained hereinafter.

An example of the present separation system will be explained with a figure.

FIG. 1 illustrates a separation system comprising a container "1" capable of holding a solution, an anion-exchange membrane "4" which separates the container "1" into a material feed-cell "2" and a permeation cell "3", a cathode "5" and an anode "6" which are respectively provided in the cells, DC power supplies "7" and "8" which are respectively connected to the electrodes.

In this case, in order to increase the surface area of the ion-exchange membrane "1" and to improve the separation speed, it can be advantageously feasible to separate the container into 3 or more cells, preferably 50–5,000 cells, by providing in the container at least a pair of cation- and anion-exchange membranes at a prescribed distance in addition to or in place of the anion-exchange membrane "1" in order to alternately form material feed-cells and permeation cells, and providing electrodes in the cells of both ends of the container.

In other words, a separation system, which comprises a container capable of holding a solution, at least a pair of cation- and anion-exchange membranes which are provided at a prescribed distance in the container to separate the container into a material feed-cell and a permeation cell, a pair of anode and cathode which are provided in the cells of both ends of the container, as well as being provided apart from the membranes, and a DC power supply connected to the electrodes, is extremely favorable as an industrial-scale separation system for the present preparation of a high α-glycosyl-L-ascorbic acid content product.

The present separation system can be used in a single-stage or multi-stage to meet to final use.

For example, a double-stage separation system is usually employed when an aqueous solution containing at least 3 ingredients of α-glycosyl-L-ascorbic acid, L-ascorbic acid and a saccharide is used as a material feed-solution.

A high α-glycosyl-L-ascorbic acid content product is prepared by subjecting a material solution to electrodialysis wherein an ion-exchange membrane selected from those having a molecular weight cut-off in the range of about 100–200 is used in order to predominantly pass L-ascorbic acid through the membrane from a material feed-cell to a first permeation cell and to remain α-glycosyl-L-ascorbic acid and saccharides in the material feed-cell; and separating the resultant α-glycosyl-L-ascorbic acid from saccharides by subjecting the resultant aqueous solution in the material feed-cell as a material feed-solution to electrodialysis wherein an anion-exchange membrane selected from those having a molecular weight cut-off of about 200–1,000 is used in order to remain saccharides in the material feed-cell and to predominantly pass α-glycosyl-L-ascorbic acid through the membrane from the material feed-cell to a second permeation cell.

Such a double-stage separation system can be feasible in the reverse order, if necessary: H can be effected by placing a material solution in a first material-feed cell, subjecting the material solution to electrodialysis wherein an anion-exchange membrane selected from those having a molecular weight cut-off in the range of about 200–1,000 is used in order to predominantly pass α-glycosyl-L-ascorbic acid and L-ascorbic acid through the membrane from the first material feed-cell to a first permeation cell, and subjecting the resultant aqueous solution held in the first permeation cell as a second material feed-solution to electrodialysis wherein an anion-exchange membrane selected from those having a molecular weight cut-off in the range of about 100–200 is used in order to remain α-glycosyl-L-ascorbic acid held in the second material feed-cell, and to predominantly pass L-ascorbic acid through the membrane from the second material feed-cell to a second permeation cell.

The use of the present separation system can be dependently changed on the main ingredients of a material feed-solution, as well as on the final use of the resultant high α-glycosyl-L-ascorbic acid content product.

Usually, a single-stage separation system can be employable for a material feed-solution containing 2 main ingredients of α-glycosyl-L-ascorbic acid and L-ascorbic acid or a saccharide, as well as for a material feed-solution containing 3 main ingredients of α-glycosyl-L-ascorbic acid, L-ascorbic acid and a saccharide when the coexisting L-ascorbic acid or saccharide does not hinder the final use of the resultant high α-glycosyl-L-ascorbic acid content product.

It is preferable to remove concomitants present in a precrystallization solution as much as possible in order to obtain a crystalline 2-O-α-D-glucopyranosyl-L-ascorbic acid as a high α-glycosyl-L-ascorbic acid content product.

When a high α-glycosyl-L-ascorbic acid content product obtainable by the present separation system is an aqueous solution of a high 2-O-α-D-glucopyranosyl-L-ascorbic acid in the form of free acid, the aqueous solution is readily crystallized after concentrated into a supersaturated solution, and because of this a crystalline 2-O-α-D-glucopyranosyl-L-ascorbic acid is recovered in a relatively-high yield.

When a high α-glycosyl-L-ascorbic content product obtainable by the present separation system is a mixture of α-glycosyl-L-ascorbic acids having one or more coupled α-glycosyl groups as shown in formula 1, the product can be advantageously hydrolyzed by glucoamylase (EC 3.2.1.3) into 2-O-α-D-glucopyranosyl-L-ascorbic acid and D-glucose, and the resultant mixture is purified by the present separation system, or, if necessary purified by adsorption and desorption wherein an anion-exchange resin is used or by column chromatography. Thus, an aqueous solution of a high-purity 2-O-α-D-glucopyranosyl-L-ascorbic acid is obtained, and which is then concentrated into a supersaturated solution to effect crystallization, followed by recovering the resultant crystalline 2-O-α-D-glucopyranosyl-L-ascorbic acid.

The high α-glycosyl-L-ascorbic acid content products thus obtained can be advantageously incorporated as a vitamin C-enriched agent having a satisfiable stability and safeness, as well as a taste-improving agent, acid-imparting agent, stabilizer, quality-improving agent, antioxidant and uv-absorbent, in food products, cigarettes, tobaccos, feeds and pet foods, prophylactic and therapeutic agents for susceptive-diseases such as viral diseases, bacterial diseases and malignant tumors, and cosmetics such as skin-refining agents and skin-whitening agents. The amount of the incorporated α-glycosyl-L-ascorbic acid in the above products is at least 0.001 w/w % (the symbol "w/w %" is abbreviated as "%" in the specification unless "%" is specified otherwise).

When the α-glycosyl-L-ascorbic acid according to the present invention is in the form of free acid, it can be reacted with metal hydroxides and/or metal carbonates to form a salt such as a sodium salt, calcium salt, magnesium salt, ferric salt, ferrous salt, copper salt and zinc salt, which is then adjusted its pH to obtain a product having a vitamin C activity and a mineral-enriching activity. The products thus obtained can be also advantageously used in food products, pharmaceuticals and cosmetics.

The following experiments will explain the present invention.

EXPERIMENT 1

Separation of α-glycosyl-L-ascorbic acid and L-ascorbic acid

Five ml of an aqueous solution (pH 4.5) as a material feed-solution containing 250mg 2-O-α-D-glucopyranosyl-L-ascorbic acid and 250mg L-ascorbic acid was electrodialyzed at 3.4 volts by using "Microacilyzer Gi", a portable desairing apparatus commercialized by Asahi Chemical Industry Co., Ltd., Tokyo, Japan, equipped with "Aciplex Cartridge AC-110-10" comprising a cation-exchange membrane and an anion-exchange membrane, both of which have a molecular weight cut-off of about 100 and a surface area of about 10cm$^2$.

The residual percentages of 2-O-α-D-glucopyranosyl-L-ascorbic acid and L-ascorbic acid in a material feed-cell were measured at a prescribed time-interval.

The results were as shown in Table 1.

TABLE 1

| Time (minute) | 2-O-α-D-Glucopyranosyl-L-ascorbic acid (%) | L-Ascorbic acid (%) |
| --- | --- | --- |
| 0 | 100 | 100 |
| 30 | 98 | 69 |
| 60 | 96 | 37 |
| 90 | 94 | 10 |
| 120 | 91 | 0 |

As evident from the results in Table 1, L-ascorbic acid predominantly permeated the anion-exchange membrane from the material feed-cell, and this was also confirmed by the data obtained from the permeation cell.

EXPERIMENT 2

Separation of α-glycosyl-L-ascorbic acid and saccharide

Five ml of an aqueous solution (pH 5.0) as a material feed-solution, which contained 250mg 2-O-α-D-glucopyranosyl-L-ascorbic acid and 250mg maltose, both of which had almost the same molecular weight, was electrodialyzed similarly as in Experiment 1 by using "Microacilyzer Gi", a portable desalting apparatus commercialized by Asahi Chemical Industry Co., Ltd., Tokyo, Japan, equipped with "Aciplex Cartridge AC-110-10" comprising a cation-exchange membrane having a molecular weight cut-off of about 100 and an anion-exchange membrane having a molecular weight cut-off of about 300, both of which have a surface area of about 10cm$^2$.

The residual percentages of 2-O-α-D-glucopyranosyl-L-ascorbic acid and L-ascorbic acid held in a material feed-cell were measured at a prescribed time-interval.

The results were as shown in Table 2.

TABLE 2

| Time (minute) | 2-O-α-D-Glucopyranosyl-L-ascorbic acid (%) | Maltose (%) |
| --- | --- | --- |
| 0 | 100 | 100 |
| 30 | 58 | 96 |
| 60 | 33 | 94 |
| 90 | 9 | 91 |

As evident from the results in Table 2, 2-O-α-D-glucopyranosyl-L-ascorbic acid predominantly permeated the anion-exchange membrane from the material feed-cell, and this was also confirmed by the data obtained from the permeation cell.

EXPERIMENT 3

Separation of α-glycosyl-L-ascorbic acid and saccharide

Seven and half ml of an aqueous solution (pH 4.5) as a material feed-solution which contained 250mg 2-O-α-D-glucopyranosyl-L-ascorbic acid and 250mg maltose, was subjected to a double-stage electrodialysis.

According to the method in Experiment 1, the aqueous solution was electrodialyzed by using a portable desairing apparatus equipped with "Aciplex cartridge AC-110-10".

As a result, L-ascorbic acid predominantly permeated a membrane similarly as in Experiment 1, and 100% L-ascorbic acid permeated into a permeation cell 120 minutes after the initiation of electrodialysis. Maltose and 2-O-α-D-glucopyranosyl-L-ascorbic acid were remained in a material feed-cell at residual percentages of 98% and 91% respectively.

Accordingly, the purity of 2-O-α-D-glucopyranosyl-L-ascorbic acid in the material feed-cell increased from about 33% to about 48%.

According to the method in Experiment 2, the resultant solution in the material feed-cell as a material feed-solution was electrodialyzed by using a portable desairing apparatus equipped with "Aciplex cartridge AC-120-10".

As a result, similarly as in Experiment 2 2-O-α-D-glucopyranosyl-L-ascorbic acid predominantly permeated a membrane, and the data obtained 90 minutes after the initiation of electrodialysis indicated that the purity of 2-O-α-D-glucopyranosyl-L-ascorbic acid in a permeation cell was about 90% and the yield was about 83% against the 2-O-α-D-glucopyranosyl-L-ascorbic acid in the material feed-solution.

All the ingredients such as 2-O-α-D-glucopyranosyl-L-ascorbic acid, L-ascorbic acid and maltose were stable during the electrodialysis without causing an unnecessarily decomposition.

Examples of the present invention will be described hereinafter.

EXAMPLE 1

Preparation of high α-glycosyl-L-ascorbic acid content product

Three parts by weight of dextrin was dissolved in 5 parts by weight of water while heating, and the resultant mixture was added with 2 parts by weight of L-ascorbic acid, adjusted to pH 5.5, heated to 60° C, and further added with 400 units/g dextrin of cyclomaltodextrin glucanotransferase commercialized by Hayashibara Biochemical Laboratories Inc., Okayama, Japan, based on the weight of the dry solid (d.s.b.), and subjected to an enzymatic reaction for 24 hours.

High-performance liquid chromatography (HPLC) analysis of the reaction mixture revealed that it contained about 40% α-glycosyl-L-ascorbic acids such as 2-O-α-D-glucopyranosyl-L-ascorbic acid, 2-O-α-D-maltosyl-L-ascorbic acid, 2-O-α-D-maltotriosyl-L-ascorbic acid, 2-O-α-D-maltotetraosyl-L-ascrobic acid, and 2-O-α-D-maltopentaosyl-L-ascorbic acid.

The reaction mixture was treated with a UF-membrane to remove the remaining enzyme, and the permeated solution was decolored and filtered with an activated charcoal to obtain a 300 ml filtrate having a 90 g solid matter, d.s.b. The filtrate was electrodialyzed by using "Microacilyzer G3", a portable desalting apparatus commercialized by Asahi Chemical Industry Co., Ltd., Tokyo, Japan, equipped with "Aciplex Cartridge AC-110-400" comprising a cation-exchange membrane and an anion-exchange membrane, both of which have a molecular weight cut-off of about 100 and a surface area of about 400 cm$^2$ and by using 0.5N in a sodium nitrate as an electrolytic solution for electrode cells.

The electrodialysis was started from 11.6 volts and then decreased stepwisely as the increase of the specific electric resistance of a solution held in a material feed-cell.

The L-Ascorbic acid predominantly permeated the anionexchange membrane, and about 98% L-ascorbic acid and a slight amount of α-glycosyl-L-ascorbic acid permeated the membrane about 7 hours after the initiation of the electrodialysis.

As a result, a solution containing substantially whole amount of α-glycosyl-L-ascorbic acid and saccharides from the material feed-cell was recovered, and a high α-glycosyl-L-ascorbic acid content product with a purity of 48% was obtained.

The yield was about 95% or higher against the α-glycosyl-L-ascorbic acid in the material feed-solution, d.s.b.

The product has a satisfiable stability and physiological activity, and these render it advantageously useful in food products, pharmaceuticals and cosmetics as a vitamin C-enriched agent, stabilizer, quality-improving agent, antioxidant, taste-improving agent, biological activator and uv-absorbent.

No apparent decrease of separation performance caused by fouling was observed even after a 20-times repeated use of the electrodialysis with the desalting apparatus in this example.

EXAMPLE 2

Preparation of high α-glycosyl-L-ascorbic acid content product

Similarly as in Example 1, an enzyme remained in an enzymatic reaction mixture obtained by the method in Example 1 was removed, and the resultant solution was decolored and filtered with an activated charcoal to obtain a 300 ml filtrate having a 90 g solid matter, d.s.b., which was then electrodialyzed in accordance with the method in Example 1 by using "Microacilyzer G3", a portable desairing apparatus commercialized by Asahi Chemical Industry Co., Ltd., Tokyo, Japan, equipped with "Aciplex Cartridge AC-130-400" comprising a cation-exchange membrane having a molecular weight cut-off of about 100 and an anion-exchange membrane having a cut-off of about 1,000, both of which have a surface area of about 400cm$^2$.

The α-Glycosyl-L-ascorbic acid and L-ascorbic acid predominantly permeated the anion-exchange membrane, and a substantially whole amount of L-ascorbic acid and α-glycosyl-L-ascorbic acid with an improved purity was recovered from a permeation cell, The resultant mixture recovered from the permeation cell was dried in vacuo and pulverized into a high α-glycosyl-L-ascorbic acid content powder.

The yield of the powder was about 90% or higher against the α-glycosyl-L-ascorbic acid in the material feed-solution, d.s.b.

Although the product exhibits a direct reducing activity inherent to the coexisting L-ascorbic acid, it substantially has the inherent properties of α-glycosyl-L-ascorbic acid, and, similarly as the product in Example 1, it can be advantageously used in a wide variety of fields such as food products, pharmaceuticals and cosmetics.

No apparent decrease of separation performance caused by fouling was observed even after a 20-times repeated use of the electrodialysis with the desalting apparatus in this example.

EXAMPLE 3

Preparation of high α-glycosyl-L-ascorbic acid content product

A high α-glycosyl-L-ascorbic acid content powder, prepared by the method in Example 2, was dissolved in water into an about 20% aqueous solution which was then electro-dialyzed similarly as the method in Example 1 by using "Microacilyzer G3", a portable desalting apparatus commercialized by Asahi Chemical Industry Co., Ltd., Tokyo, Japan, equipped with "Aciplex Cartridge AC-110-400" comprising a cation-exchange membrane and an anion-exchange membrane, both of which have a molecular weight cut-off, about 100, and a surface area, about 400cm$^2$.

Similarly as in Example 1, L-ascorbic acid predominantly permeated, and a α-glycosyl-L-ascorbic acid with an improved purity of about 70%, d.s.b., was recovered from a material feed-cell. Thus, a high α-glycosyl-L-ascorbic acid content liquid was obtained.

Similarly as the product in Example 1, the product has a satisfiable stability, and this renders it advantageously useful in a wide variety of fields such as food products, pharmaceuticals and cosmetics.

EXAMPLE 4

Preparation of high α-glycosyl-L-ascorbic acid content product

A solution containing a high α-glycosyl-L-ascorbic acid content product, prepared by an enzymatic reaction and electrodialysis according to the method in Example 1, was heated to 55° C., adjusted to pH 4.5, added with 10 units/g of glucoamylase, d.s.b., and subjected to an enzymatic reaction at the temperature and pH for 24 hours in order to convert α-glycosyl-L-ascorbic acid into 2-O-α-D-glucopyranosyl-L-ascorbic acid.

The reaction mixture was heated to inactivate the remaining glucoamylase, decolored and filtered with an activated charcoal. The resultant filtrate was fed to a column packed with a cation-exchange resin ($H^+$) to effect demineralization, and the resultant solution was fed to a column packed with an anion-exchange resin ($OH^-$) to adsorb anions on thereon. The column packed with the anion-exchange resin was washed with water to remove glucose, and fed with 0.5N hydrochloric acid to effect elution, followed by recovering a high 2-O-α-D-glucopyranosyl-L-ascorbic acid content fraction.

The fraction was concentrated in vacuo into an about 73% solution which was then placed in a crystallizer, added with a seed crystal, heated to 40° C., and gradually cooled to 15° C. over a period of 2 days under a gentle-stirring condition. The resultant mixture was separated by a basket-type centrifuge, and the resultant crystal was recovered after spraying it with a small amount of water.

The product was a high-purity crystalline 2-O-α-D-glucopyranosyl-L-ascorbic acid which exhibits no direct reducing activity but has a satisfiable stability and physiological activity. The product can be advantageously used in a wide variety of fields such as food products, pharmaceuticals and cosmetics as a vitamin C-enriched agent, stabilizer, quality-improving agent, antioxidant, physiological activator and uv-absorbent.

As described above, the present invention has features: In the present preparation of a high α-glycosyl-L-ascorbic acid content product from an aqueous solution containing a-glycosyl-L-ascorbic acid together with L-ascorbic acid and/or a saccharide, the aqueous solution is subjected to electrodialysis wherein an anion-exchange membrane is used in order to allow the L-ascorbic acid to predominantly permeate the membrane and separate the L-ascorbic acid from the α-glycosyl-L-ascorbic acid; or in order to allow the α-glycosyl-L-ascorbic acid to predominantly permeate the membrane and to separate the α-glycosyl-L-ascorbic acid from the saccharide. Thus, a high α-glycosyl-L-ascorbic acid content product is readily prepared at a relatively-high concentration and in a relatively-high yield.

The present invention requires no eluate and regeneration agent and cuts the amount of water.

Because of these, a solution which contains α-glycosyl-L-ascorbic acid is not unnecessarily diluted.

Thus, the present invention has great advantages in an industrial-scale preparation of α-glycosyl-L-ascorbic acid.

It is also favorable that no unnecessarily decomposition of substances would occur during electrodialysis.

The α-glycosyl-L-ascorbic acid content product thus obtained has a satisfiable stability and physiological activity, and these render it advantageously useful in a variety of fields such as food products, pharmaceutical and cosmetics as a vitamin C-enriched agent, stabilizer, quality-improving agent, antioxidant, taste-improving agent, physiological activator and uv-absorbent.

Accordingly, the present preparation of a high α-glycosyl-L-ascorbic acid content product and the separation system for said preparation have a great significance in a wide variety of fields such as food products, pharmaceuticals and cosmetics.

While there has been described what is at present considered to be the preferred embodiments of the invention, it will be understood the various modifications may be made therein, and it is intended to cover in the appended claims all such modifications as fall within the true spirits and scope of the invention.

We claim:

1. A process for preparing an α-glycosyl-L-ascorbic acid containing product, which comprises:
   (a) subjecting an aqueous solution containing α-glycosyl-L-ascorbic acid and L-ascorbic acid and optionally a saccharide to electrodialysis through a first anion-exchange membrane having a molecular weight cut-off in the range of about 100–200 to allow said L-ascorbic acid to predominantly permeate said first membrane and to separate said L-ascorbic from α-glycosylL-ascorbic acid, and when said saccharide is present also through a second anion-exchange membrane having a molecular weight cut-off in the range of about 200–1,000 to allow said α-glycosyl-L-ascorbic acid to predominantly permeate said second membrane and to separate said α-glycosyl-L-ascorbic acid from said saccharide; and
   (b) recovering the resultant α-glycosyl-L-ascorbic acid containing product.

2. The process of claim 1, wherein the step (a) is effected at pH 8 or lower.

3. The process of claim 1, wherein said first anionexchange membrane is used together with a cation-exchange membrane.

4. The process of claim 1, wherein said αglycosyl-L-ascorbic acid is 2-O-α-D-glucopyranosyl-L-ascorbic acid.

5. The process of claim 1, further comprising, after step (a) and before step (b), a step of concentrating the resultant aqueous solution containing α-glycosyl-L-ascorbic acid obtained in the step (a) into a supersaturated solution, and allowing the supersaturated solution to effect crystallization of α-glycosyl-L-ascorbic acid.

6. The process of claim 5, wherein said α-glycosylL-ascorbic acid is 2-O-α-D-glucopyranosyl-L-ascorbic acid.

7. The process of claim 1, wherein said α-glycosyl-L-ascorbic acid containing product obtained in step (b) is substantially free of L-ascorbic acid.

8. The process of claim 1, wherein said L-ascorbic acid is a member selected from the group consisting of L-ascorbic acids in the form of free acid, alkaline metal salts, alkaline-earth metal salts and mixtures thereof.

9. The process of claim 1, wherein said saccharide is present in said aqueous solution.

10. The process of claim 9, wherein said second anionexchange membrane is used together with a cation-exchange membrane.

* * * * *